US010245008B2

(12) United States Patent
Paige

(10) Patent No.: US 10,245,008 B2
(45) Date of Patent: Apr. 2, 2019

(54) BODILY FLUIDS SPECIMEN COLLECTION DEVICE

(71) Applicant: Susan D. Paige, Harrison, MT (US)

(72) Inventor: Susan D. Paige, Harrison, MT (US)

(73) Assignee: Susan D. Paige, Harrison, MT (US)

( * ) Notice: Subject to any disclaimer, the term of this patent is extended or adjusted under 35 U.S.C. 154(b) by 363 days.

(21) Appl. No.: 15/204,043

(22) Filed: Jul. 7, 2016

(65) Prior Publication Data

US 2018/0008238 A1    Jan. 11, 2018

(51) Int. Cl.
*A61B 10/00* (2006.01)
*A61B 5/15* (2006.01)

(52) U.S. Cl.
CPC ........ *A61B 10/007* (2013.01); *A61B 5/15003* (2013.01); *A61B 5/150045* (2013.01); *A61B 10/0038* (2013.01); *A61B 10/0058* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,560,199 A * | 7/1951 | Trichel | ............... | A61B 10/0038 4/144.1 |
| 2,603,795 A | 7/1952 | Terlizzi | | |
| 4,203,169 A | 5/1980 | Dale | | |
| 5,146,637 A * | 9/1992 | Bressler | ............... | A61B 10/007 141/372 |
| 5,202,094 A * | 4/1993 | Jones | ................. | A47G 23/0216 16/111.1 |
| 6,434,762 B2 * | 8/2002 | Gordon | ............. | A61B 10/0038 4/315 |
| D489,453 S | 5/2004 | Sapyt | | |
| 6,811,754 B2 | 11/2004 | House | | |
| 7,011,634 B2 | 3/2006 | Paasch | | |
| 8,079,562 B1 | 12/2011 | Denman | | |
| 8,091,848 B1 * | 1/2012 | Reed | .................... | A61B 10/007 220/737 |
| 8,297,577 B1 | 10/2012 | Denman | | |
| 2002/0179794 A1 * | 12/2002 | Yang | .................... | A61B 10/007 248/311.2 |
| 2003/0021735 A1 * | 1/2003 | House | .................. | A61B 10/007 422/547 |
| 2006/0184064 A1 * | 8/2006 | Paasch | ................. | A61B 10/007 600/573 |
| 2017/0086728 A1 * | 3/2017 | Hidas | .................. | A61B 5/0022 |

\* cited by examiner

*Primary Examiner* — Christopher R Harmon
(74) *Attorney, Agent, or Firm* — MacBride Law, PLLC; William L. MacBride, Jr.

(57) ABSTRACT

The invention is a bodily fluids sample collection device comprising a planar elastic elongated frame member and has frame sides concurrently angling inward to a cup securing region, thereby having an increasingly narrowing frame width to a semi-circular cup holding portion, adapted to securely receive a bodily fluids sample cup disposed in an upright position for receiving a bodily fluids sample from a patient, and flexibly adapted for easy placement and release of the bodily fluids sample cup. The toilet bowl or the toilet seat freely supports the device, and handles enables the patient to grasp the device without touching the toilet seat or the toilet bowl, and away from the sample cup of differing sizes. The device may have a collection handle, enabling the patient to grasp the device away from the bodily fluids sample cup.

20 Claims, 8 Drawing Sheets

BODILY FLUIDS SPECIMEN COLLECTION DEVICE

FIELD OF THE INVENTION

This application relates to a bodily fluids sample collection device for a patient or other user to collect or receive a specimen of urine or other excrement from the patient's body, in a cup or other receptacle without contamination, with or without a support structure such as a toilet bowl.

BACKGROUND OF THE INVENTION

A clinical issue that has been concerning medical facilities for many years is how best to obtain a sterile urine, semen, soft stool, menses blood or other excrement biological sample, of bodily fluid from a patient. There is no American Medical Association standard policy or protocol for conducting bodily fluids sample collection.

Typically, the patient at a medical office is handed a urine sample cup and told to go into a restroom and urinate, filling that urine sample cup while it is being held in the patient's hand. A urine sample, in particular, is required to be free of bacteria which may collect around the exit to the bladder, in urinary passages, or exist on the patient's hands. In order to eliminate infecting the sample with the bacteria from the bladder or urinary passages, a mid-stream sample is requested to be collected, excluding the first part of a urine stream from the sample. The patient, therefore, must commence urinating before collecting the sample. Collecting a mid-stream sample may be difficult for many people.

Doctors, clinics, clinicians, nurses, parents, lab technician, other medical practitioners or caregivers, hospitals, prisons, senior centers, military facilities, rehab centers, disabled adult homes, and other employment testing situations (collectively, plural, "medical service provider"), potentially all need, at some time, to collect sterile urine samples. It is nearly impossible to maintain a sterile field or environment when the patient is holding the sample cup in their hand. There is no known technology being used to solve the problem of a patient maintaining a sterile field for a "clean catch", particularly for women patients.

Patients having special needs; such as the elderly, obese or disabled, children, or pregnant women; have problems collecting such samples in the manner typically utilized. There is almost no way to do this without having the patient, the user, contaminating the sample cup and/or the actual bodily fluids sample. The device must be freely maneuverable, and able to easily receive and release sample receptacles, to be convenient for both the medical service provider and the patient.

While there are devices in the related art which can be mounted within a toilet bowl, utilizing the toilet bowl or seat as support, and have a receptacle for receiving a sample, there has been a need for such device that is freely maneuverable and usable with variously sized, commonly used receptacles. Devices which require installation within the toilet bowl, between the bowl and the toilet seat are not so maneuverable, awkward to use and to retrieve the sample receptacle, with the potential of losing or contaminating the sample.

Urine sample collection devices are known which have multiple parts, complicating their use and placement on or within a toilet, and utilize sample receptacles which are not the standard, plastic, disposable and sterile urine sample cups routinely used in medical offices, clinics and other locations where urine samples are frequently taken, requiring numerous receptacles. Some devices may provide for a standard sample cup or jar, but collect the sample in a reused collection section prior to collection in a jar. Even if reusable, these additional collection elements cause more waste material for disposal. As well, those devices may require the use of the toilet bowl as a support structure, causing the medical service provider or the patient to handle the toilet seat for installation and/or removal of the device. This known art does not provide for a sanitary sample collection procedure.

The bodily fluids collection devices described in the related art do not disclose features of the present invention and would not be as suitable for the required purpose of the present invention hereinafter described. Urine collection devices are well known in the related art, exemplified by U.S. Pat. No. 7,011,634 to Paasch et al ("Paasch"); U.S. Pat. Nos. 8,079,562 and 8,297,577, both to Denman (collectively, "Denman"); U.S. Pat. No. 6,811,754 to House ("House"); U.S. Pat. No. D489,453 to Sapyta ("Sapyta")' U.S. Pat. No. 42,032,169 to Dale ("Dale"); and U.S. Pat. No. 2,603,795 to Terlizzi ("Terlizzi"). Terlizzi does not disclose a removable urine sample cup, and neither Terlizzi, nor Dale teaches the use of a standard, plastic urine sample cup, for sample cups commonly used in the industry. Paasch and House disclose the use of additional sample collection trays along with a sample cup. None of the known devices except for House, disclose collecting the bodily fluids sample directly into a standard bodily fluids sample cup or jar. Dale, as well, is not mobile. Dale, House, Paasch, Sapyta and Denman all require use on a toilet bowl, and not the toilet seat. The present invention discloses a frame member planar from end to end, and not set within the toilet bowl. Dale, House, Paasch, Denman, and Sapyta all disclose devices that are not planar from end to end, but are set within the toilet bowl. None of the known devices disclose all the feature of the present invention where the sides of the elastic elongated frame member are angled inwardly, to facilitate engaging the bodily fluids sample cup.

None of the references contain every feature of the present invention, and none of these references in combination disclose or teach every feature of the present invention.

The foregoing and other objectives, advantages, aspects, and features of the present invention will be more fully understood and appreciated by those skilled in the art upon consideration of the detailed description of a preferred embodiment, presented below in conjunction with the accompanying drawings.

SUMMARY OF THE INVENTION

The present invention is directed to a bodily fluids sample collection device having a plastic frame used to hold a plastic bodily fluids sample collection cup, to ensure the sample remains clean and uncontaminated. Also, the present invention keeps the patient's hands clean, and saves the medical lab technician's hands from coming in contact with the bodily fluids. The present invention holds the sample cup safely and securely, allowing the sample to remain uncontaminated and the hands clean.

The present invention discloses a bodily fluids sample collection device comprising an elastic elongated frame member which is planar from the first end to the opposing second end. The first frame side and the opposing second frame side of the elastic elongated frame member are concurrently angling inward toward each other from the opposite ends of the bodily fluids sample collection device toward a cup securing region centrally located in the elastic elongated frame member, thereby having an increasingly narrowing frame width between the two frame sides toward the cup securing region. The opposing frame sides each having an opposing, flexibly adjustable semi-circular cup holding portion, comprised of a pair of opposing semi-circular cup holding portions which define the cup securing region.

The first frame side and the opposing second frame side are flexibly adapted to securely and removably engage, receive and support a bodily fluids sample cup disposed in an upright position for receiving a bodily fluids sample from a patient, and flexibly adapted for easy placement and release of the bodily fluids sample cup by the patient. The elastic elongated frame member having a frame length extending beyond an edge of a toilet bowl, whereby handles enable the patient to grasp the bodily fluids sample collection device.

In alternative embodiments of the invention, the toilet bowl freely supports the bodily fluids sample collection device along a minor axis of the toilet bowl or a major axis of the toilet bowl. The frame length of the elastic elongated frame member extends beyond minor outer edges of the toilet bowl. In an alternative embodiment, a toilet seat, hingedly attached to the toilet bowl, supports the elastic elongated frame member.

Handles enables the patient to grasp the elastic elongated frame member without touching the toilet seat or the toilet bowl and grasp the elastic frame member distally, or away from, from the bodily fluids sample cup. The bodily fluids sample cup is supported in the cup securing region and has a top located generally planarly within, and slightly above, the elastic elongated frame member and a lid being securing to the top of the bodily fluid sample cup. The pair of opposing semi-circular cup holding portions of the elastic elongated frame member are elastically adjustable to securely receive and support bodily fluids sample cups of differing sizes.

An alternative embodiment of the invention discloses an elastic elongated frame member comprising a first end and an opposing second handle end with the elastic elongated frame member further comprising a collection handle obliquely attached to the elastic elongated frame member at the opposing second handle end, and a collection handle end on the collection handle opposing the opposing second handle end. The collection handle enables the patient to grasp the bodily fluids sample collection device distally from the bodily fluids sample cup.

The present invention is easily transported, lightweight and durable. It is simple to use and inexpensive to produce and purchase. It is lightweight, making it affordable to ship. It may be disposable, or reused if sanitized.

The aforementioned features, objectives, aspects and advantages of the present invention, and further objectives and advantages of the invention, will become apparent from a consideration of the drawings and ensuing description.

BRIEF DESCRIPTION OF THE SEVERAL VIEWS OF THE DRAWINGS

The foregoing features and other aspects of the present invention are explained and other features and objects of the present invention will become apparent in the following detailed descriptions, taken in conjunction with the accompanying drawings. However, the drawings are provided for purposes of illustration only, and are not intended as a definition of the limits of the invention.

FIG. 5A illustrates the cross section front elevation view of the elastic elongated frame member at section C-C', depicting a view of the plurality of top flange members to the elastic elongated frame member, in another embodiment of the present invention.

DETAILED DESCRIPTION OF THE INVENTION

The present invention will now be described more fully hereinafter with references to the accompanying drawings, in which the preferred embodiment of the invention is shown. This invention may, however, be embodied in different forms, and should not be construed as limited to the embodiments set forth herein. Rather, the illustrative embodiments are provided so that this disclosure will be thorough and complete, and will fully convey the scope of the invention to those skilled in the art. It should be noted, and will be appreciated, that numerous variations may be made within the scope of this invention without departing from the principle of this invention and without sacrificing its chief advantages. Like numbers refer to like elements throughout.

Figures 1, 1A:
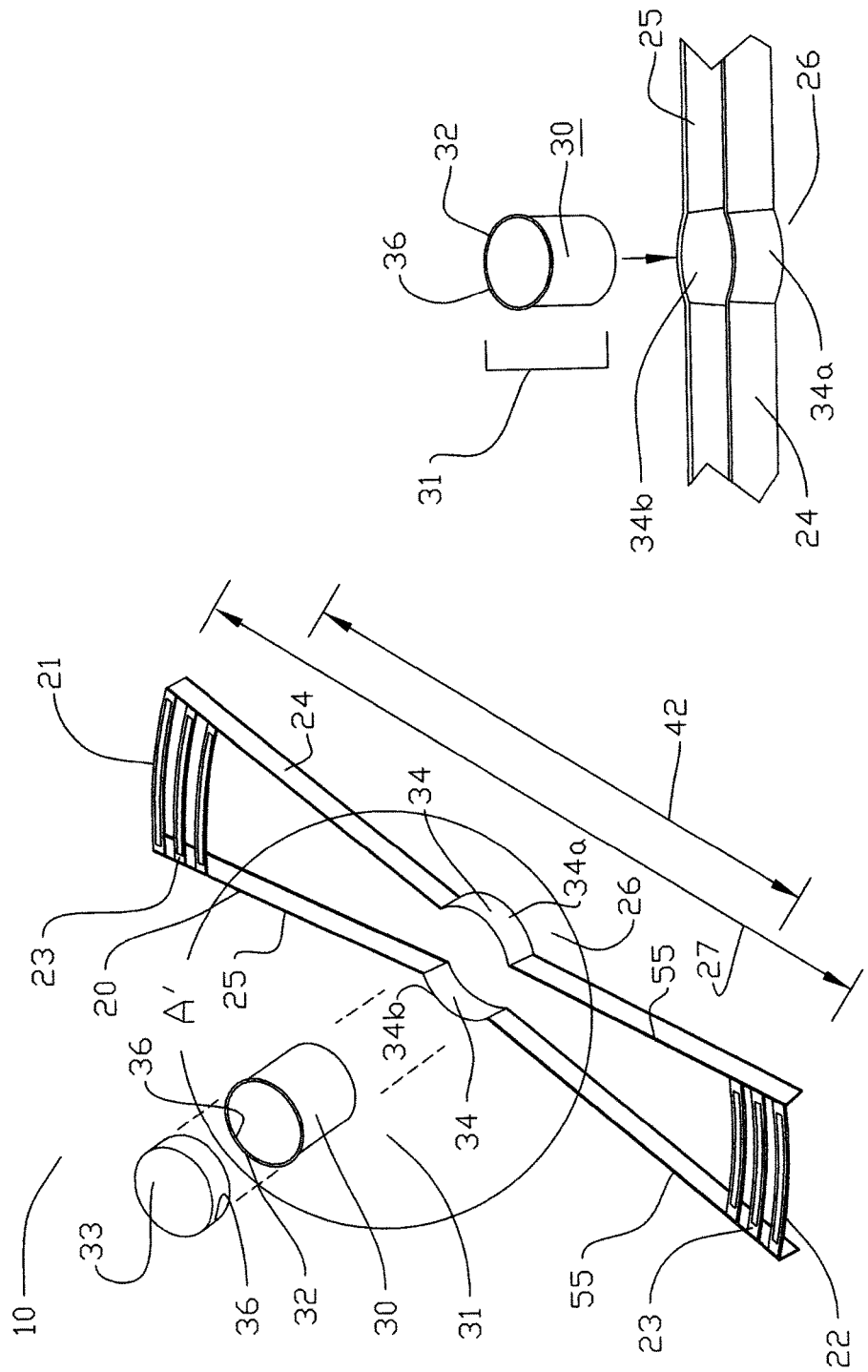
FIG. 1 illustrates a perspective elevation view of one embodiment of the present invention, depicting the bodily fluids sample collection device engaging a bodily fluids sample cup, shown in an exploding configuration and having cutout FIG. 1A'.
FIG. 1A' illustrates in cutout A' a perspective elevation, detailed view, of the cup securing region of the elastic elongated frame member having a pair of opposing semi-circular cup holding portions engaging the bodily fluids sample cup, in one embodiment of the present invention.
Figure 2:
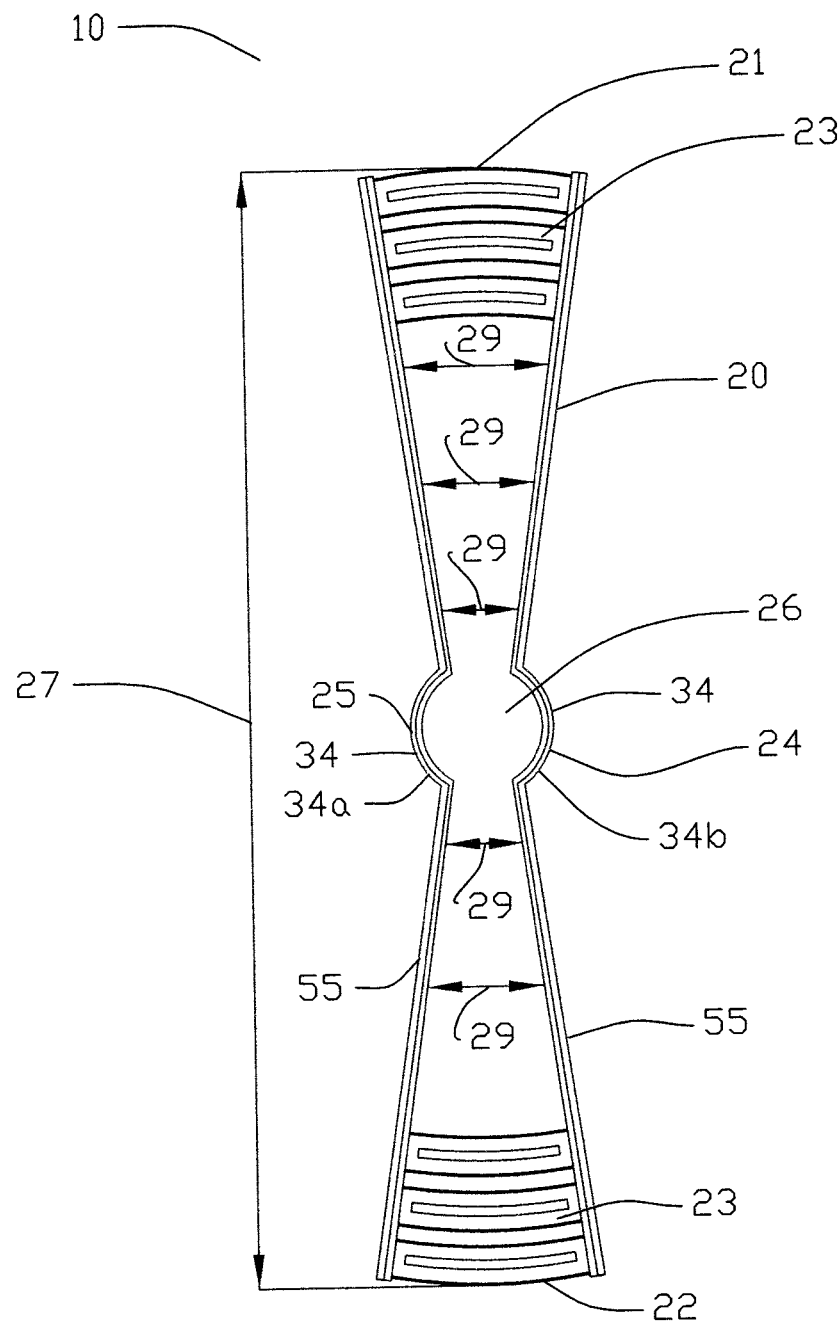
FIG. 2 illustrates a top plan view of the bodily fluids sample collection device in one embodiment of the present invention.

Turning now in detail to the drawings in accordance with the present invention, one embodiment of the present invention is depicted in FIGS. 1 and 2, perspective elevation and top plan views, respectively, of a bodily fluids sample collection device 10, comprising an elastic elongated frame member 20 having a first end 22 and an opposing second end 21, the first end 22 and the opposing second end 21 each having a handle 23. The elastic elongated frame member 20 further comprises a top edge 55, and a first frame side 24 and an opposing second frame side 25, the first frame side 24 and the opposing second frame side 25 concurrently angling inward from the first end 22, meaning in the present invention toward each other, and the opposing second end 21, respectively, from each handle 23 toward a cup securing region 26, which is centrally located in the elastic elongated frame member 20, and the first frame side 24 and the opposing second frame side 25 causing the elastic elongated frame member 20 to have, thereby, an increasingly narrowing frame width 29 (depicted in FIG. 2) between the first frame side 24 and the opposing second frame side 25. FIG. 1 illustrates an exploding configuration of the bodily fluids collection device 10 engaging a bodily fluids sample cup 30 within the cup securing region 26. The top edge 55 of the elastic elongated frame member 20 is located on the first frame side 24 and the opposing second frame side 25, and runs from the cup securing region 26 to each, respective handle 23 of the bodily fluids collection device 10.

Figure 3:
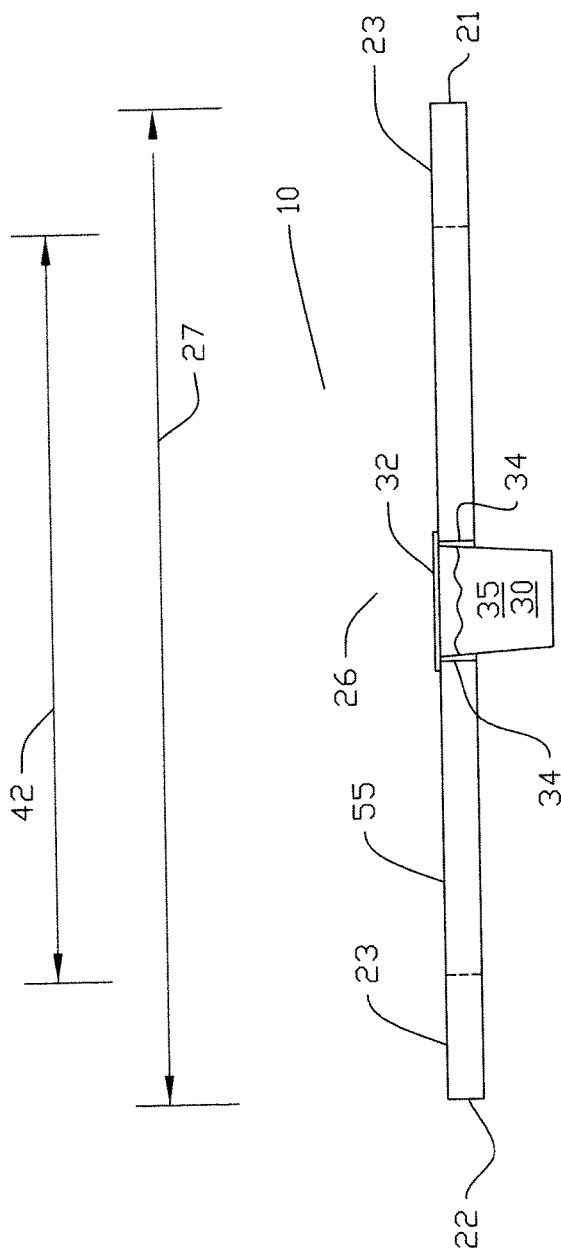
FIG. 3 illustrates a side elevation planar view of the bodily fluids sample collection device having a bodily fluids sample cup securely engaged, in one embodiment of the present invention.
Figure 4:
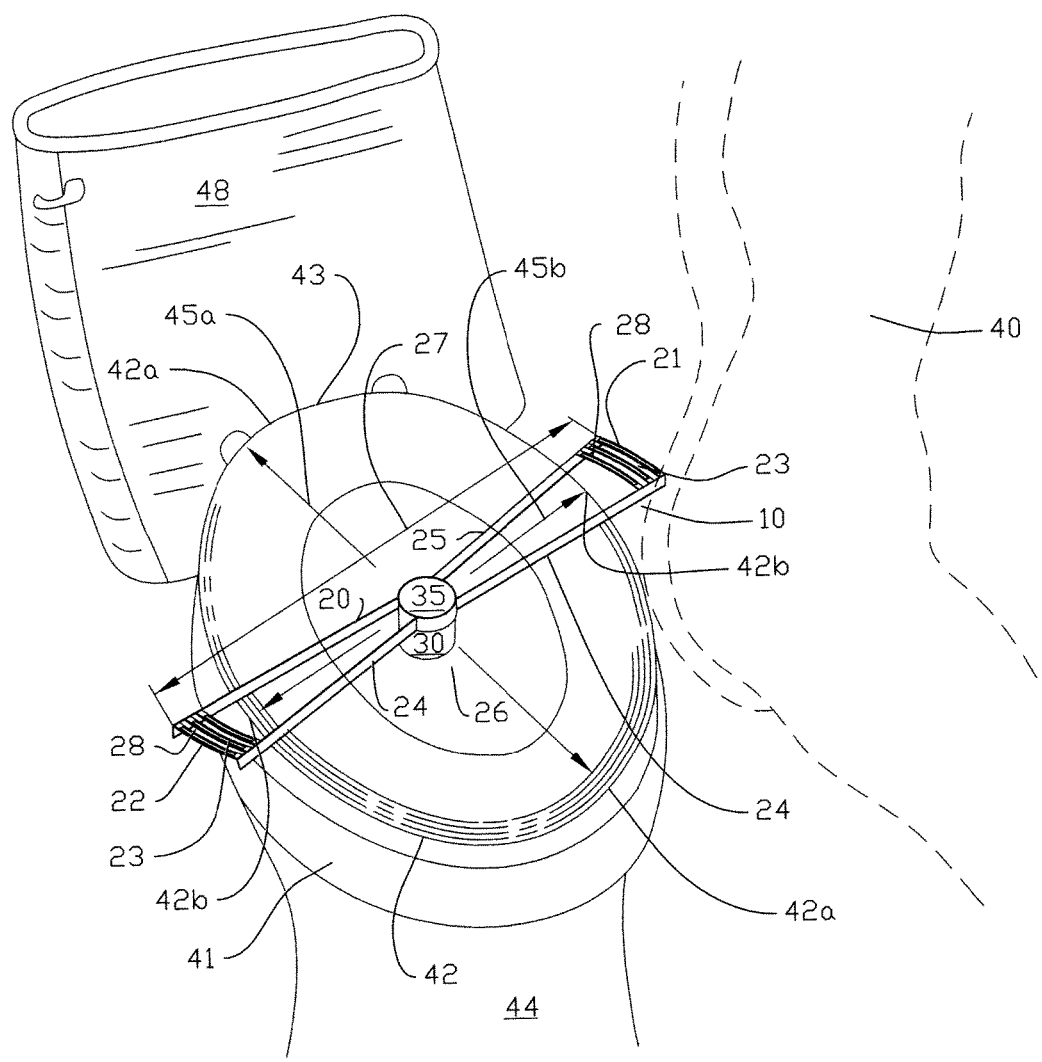
FIG. 4 illustrates a perspective view of the bodily fluids sample collection device supported by the toilet seat to a toilet bowl as used by a patient, in one embodiment of the present invention.

A pair of opposing semi-circular cup holding portions 34, shown in FIGS. 1 and 1A, defines the cup securing region 26 of the elastic elongated frame member 20. The first frame side 24 and the opposing second frame side 25 at the cup securing region 26 each have an opposing semi-circular cup holding portion (34a and 34b, respectively) of the pair of opposing semi-circular cup holding portions 34. The inward angling or slanted configuration of the first frame side 24 and opposing second frame side 25 to the elastic elongated frame member 20, shown in FIGS. 1, 2, and 4-7, provides structural support for securing and holding the bodily fluids sample cup 30 when the bodily fluids sample cup 30 (shown in FIGS. 1, 1A, 3 and 4) is filled with a bodily fluids sample 35 as depicted in FIGS. 3 and 4. The inward angling or slanted configuration of the first frame side 24 and the opposing second frame side 25 to the elastic elongated frame member 20 provides, as well, flexibility and adjustability for accommodating differing sizes of the bodily fluids sample cup 30. The bodily fluids sample cup 30 is disposed in an upright position 31 between the first frame side 24 and the opposing second frame side 25 of the elastic elongated frame member 20 for receiving the bodily fluid sample 35 from a patient 40.

As shown in FIG. 1 and in a side elevation planar view in FIG. 3, the elastic elongated frame member is planar from the first end 22 to the opposing second end 21, it being understood herein that "planar" applicable element lying in a plane or horizontal position. The bodily fluids sample cup 30 is supported in the cup securing region 26 of the elastic elongated frame member 20 and has a top 32 located generally planarly within, and slightly above, the elastic elongated frame member 20, as depicted in FIGS. 1, 1A, 3 and 4. FIG. 4 illustrate a perspective view of the bodily fluids sample collection device 10 supported by a toilet seat 43 to a toilet bowl 41 as used by a patient 40 in one embodiment of the invention. Each opposing semi-circular cup holding portion (34a and 34b) of the pair of opposing semi-circular cup holding portions 34 to the elastic elongated frame member 20 are adjustable to securely receive and support bodily fluids sample cups 30 of differing sizes. The top 32 while generally in the plane of the elastic elongated frame member 20 as depicted in FIGS. 1, 1A and 4, extends slightly above the elastic elongated frame member 20 in this and the alternative embodiments of the present invention to facilitate and accommodate attachment of a lid 33 by a fastening means 36 to the bodily fluids sample cup 30. The fastening means 36 may be opposing threads, a clip, snap-on lid or other fastening means well known in the industry. The lid 33 enable the patient 40 to close the bodily fluids sample cup 30 after removal from the bodily fluids sample collection device 10.

Figure 3A:
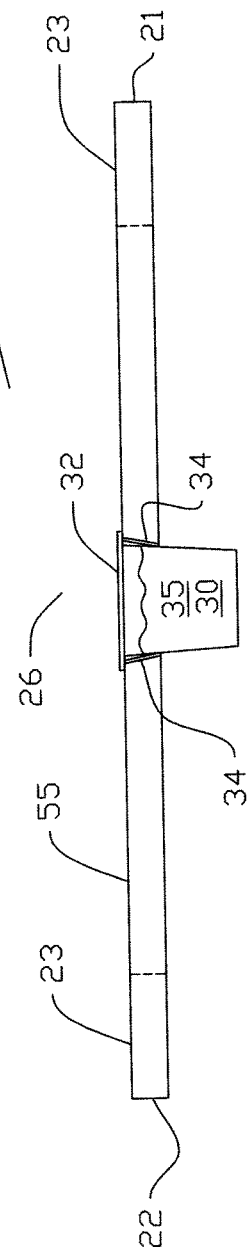
FIG. 3A illustrates a side elevation planar view of the bodily fluids sample collection device having a bodily fluids sample cup securely engaged, in an alternative embodiment of the present invention, having the pair of opposing semi-circular cup holding portions of the elastic elongated frame member inwardly sloping or slanting downward from the top edge of the elastic elongated frame member toward the cup securing region.

In an alternative embodiment of the present invention, shown in FIG. 3A, the pair of opposing semi-circular cup holding portions 34 of the elastic elongated frame member 20 are inwardly sloping or slanting downward from the top edge 55 of the elastic elongated frame member 20 toward the cup securing region 26. In this manner, the bodily fluids sample collection device 10 provides more grip or holding power applying to the bodily fluids sample cup 30.

The bodily fluids sample 35 element of the present invention may be urine, semen, soft stool, menses blood or other excrement biological sample, of bodily fluid from the patient 40.

The bodily fluids sample collection device 10 is made entirely of durable and flexible material, such as plastic, providing an elastic elongated frame member 20, allowing the elastic elongated frame member 20 to resume its normal shape spontaneously after expansion from insertion of any sized bodily fluids sample cup 30, so that the bodily fluids sample collection device 10 is maneuverable and moveable as will be demonstrated below. This construction material is lightweight, as well.

The elastic elongated frame member 20 has a frame length 27, shown in FIGS. 1-4, extending beyond an edge 42, the outside edge of the toilet bowl 41, the edge 42 being illustrated in FIG. 4. The edge 42 is understood herein, to be roughly identical with the outside edge of a toilet seat 43. One embodiment of the present invention may further comprise a toilet bowl 41 freely supporting the bodily fluids sample collection device 10, as shown in FIG. 4; however, the present invention may operate without having the toilet bowl 41 as a support. Further, the bodily fluids sample collection device 10, shown in FIGS. 1 and 4, may be comprised of the toilet bowl 41 without the toilet seat 43, allowing the patient to place the bodily fluids sample device 10 directly on the toilet bowl 41. In an alternative embodiment of the present invention, the bodily fluids sample collection device 10 is further comprised of a toilet seat 43 hingedly attached to the toilet bowl 41 and supporting the elastic elongated frame member 20, as shown in FIG. 4, allowing the patient to place the bodily fluids sample device 10 on the toilet seat 43.

The toilet bowl 41 and the toilet seat 43, illustrated in FIG. 4, are each known in the industry to cooperatively consist (in two dimensional, plane perspective), generally, of a oval shape, also known as an oblong or elliptical geometric shape, having two perpendicular axes and respective lengths, the longer of these two axes which is called a major axis 45a, and smaller of these two axes is called a minor axis 45b. The major axis 45a would correspond to and be aligned with a front 44 of the toilet bowl, as is standard in the industry as shown in FIG. 4, corresponding to and generally concurrent with the distance between major outer edges 42a of the toilet bowl 41 or the toilet seat 43, along said major axis 45a. While slight differences may exist in ovals or oval shapes of consumer purchased toilets, and size differences are recognized in the size of the consumer ovals of consumer purchased toilets with respect to toilets found in public restrooms, it is to be understood here that the bodily fluids sample collection device 10, as shown in FIGS. 1-6 is of a size to accommodate use by the patient 40 with public as well as consumer versions of the standard toilet bowl 41 and toilet seat 43.

Returning to FIG. 4, the patient 40, generally, faces front 44 on the toilet seat 43, the front 44 being an orientation of the toilet 41 opposite the flushing mechanism and hinged attachment area 48 of a standard toilet bowl and toilet seat, as generally recognized in the industry. The bodily fluids sample device 10 in one embodiment of the present invention is located on the toilet bowl 41 or toilet seat 43 along the minor axis 45b, perpendicular to the front 44 facing patient 40, which minor axis 45b corresponds to and is concurrent with the distance between minor outer edges 42b of the toilet bowl 41 or toilet seat 43 located along said minor axis 45b (which minor outer edges 42b correspond to the edge 42 of the toilet bowl 41 or toilet seat 43, along the minor axis 45b). The frame length 27 of the elastic elongated frame member 20 parallels the minor axis 45b and extends beyond the minor outer edges 42b of the toilet bowl 41 or toilet seat 43.

In another embodiment of the present invention, the bodily fluids sample device 10 may be located on the toilet bowl 41 or toilet seat 43 along the major axis 45a which corresponds to and is concurrent with the distance between major outer edges 42a of the toilet bowl 41 or toilet seat 43 along said major axis 45a (which major outer edges 42a correspond to the edge 42 of the toilet bowl 41 or toilet seat 43 along the major axis 45a). The frame length 27 of the elastic elongated frame member 20 parallels the major axis 45a and extends beyond the major outer edges 42a of the toilet bowl 41 or toilet set 43.

The patient would in this alternative embodiment, face perpendicular to the front 44 of the toilet bowl 41. The toilet bowl 41 and the toilet seat 43, acting in hinged orientation with each other, opposite the front 44, have the same orientation of major axis 45a and minor axis 45b, and essentially the same lengths of major axis 45a and minor axis 45b, respectively.

As shown in FIGS. 1, 1A and 2, and noted above, the first frame side 24 and the opposing second frame side 25 at the cup securing region 26 each have the opposing semi-circular cup holding portion (34a and 34b, respectively) of the pair of opposing semi-circular cup holding portions 34 to define the cup securing region 26 of the elastic elongated frame member 20. As depicted in FIGS. 1, 1A and 2, the semi-circular cup holding portions 34a and 34b of the pair of opposing semi-circular cup holding portions 34 are understood herein to be semi-circular portions of the respective first frame side 24 and the opposing second frame side 25 symmetrically facing each other in a concave manner. The first frame side 24 and the opposing second frame side 25 are flexibly adapted to securely and removably (as for easy placement, release, removal, and replacement) engage, receive and support a bodily fluids sample cup 30 disposed in an upright position 31 between the first frame side 24 and the opposing second frame side 25 of the elastic elongated frame member 20 for receiving a bodily fluids sample 35 from a patient 40. The increasingly narrowing frame width 29 between the first frame side 24 and the opposing second frame side 25 provides the secure restraint and reception of the flexibly adapted pair of opposing semi-circular cup holding portions 34. The bodily fluids sample device 10, in this manner, is highly and simply maneuverable, allowing the patient 40 to maneuver the bodily fluids sample collection device 10, or in other words, to securely receive and support varying sizes of a bodily fluids sample cup 30 and dispose or place it within the elastic elongated frame member 20.

Shown in FIGS. 1-8, the pair of opposing semi-circular cup holding portions 34 are flexibly adapted, providing flexibility to the elastic elongated frame member 20. With the frame width 29 of the elastic elongated frame member 20 narrower at the cup securing region 26, the pair of opposing semi-circular cup holding portions 34 provide pressure to the bodily fluids sample cup 30 to secure and support the bodily fluids cup 30 in place during use for collecting the bodily fluids sample 35 from the patient 40 and, at the same time, allow the bodily fluids sample cup 35 to be easily removed by the patient 40 or medical service provider.

The respective handles 23 of the first end 22 and the opposing second end 21 of the bodily fluids sample collection device 10, shown in FIGS. 1 and 4, enable the patient 40 to grasp the elastic elongated frame member 20 without touching the toilet seat 43 or the toilet bowl 41 and keep his or her hands away from or distally from the bodily fluids sample cup 30.

The first frame side 24 and the opposing second frame side 25 at the cup securing region 26, shown in FIG. 4, are flexibly adapted for easy placement and release of the bodily fluids sample cup 30 by the patient 40, as noted above. The frame width 29 of the elastic elongated frame member 20, therefore, is wider at the respective handles 23 than in the cup securing region 26. This configuration for the bodily fluids sample collection device 10 enables the patient, user to maneuver the bodily fluids sample device 10 easily, and place and engage any sized bodily fluids sample cup 30, as may be standardly used in the medical industry, securely within the elastic elongated frame member 20, as shown in FIGS. 1-8. Therefore, the flexible pair of opposing semi-circular cup holding portions 34 of the respective first frame side 24 and opposing second frame side 25 of the elastic elongated frame member 20 elastically yields to accommodate differing sizes of the bodily fluids sample cup 30.

As shown in FIGS. 3, the elastic elongated frame member 20 is planar from the first end 22 to the opposing second end 21, presenting the bodily fluids sample cup 30 as flush, flatly or "evenly" with the elastic elongated frame member 20 when set in place in the elastic elongated frame member 20 with the lid 33 removed, and planar, as well, to the toilet seat 43, as shown in FIG. 4. This feature of the present invention allows the patient, in an alternative embodiment of the invention, to sit on the bodily fluids sample collection device 10, or alternatively, not to do so; in either case to facilitate effective and accurate sample collecting, particularly as between the uses made by female, as compared to those made by male patients 40, as further noted below.

The lid 33 is a standard lid fitting on the respectively sized bodily fluids sample cup 30 as utilized with a particular patient 40. As depicted in FIG. 1, the lid 33 is secured to the top 32 of the bodily fluids sample cup 30 by the fastening means 36. The fastening means 36 of the lid 33 and the bodily fluids sample cup 30 may be any of fastening means known in the industry to secure lids to plastic cups, as noted above.

As depicted in FIGS. 1 and 4 of the bodily fluids sample collection device 10, each handle 23 of the respective first end 22 and the opposing second end 21 comprises a plurality of attachable handle slits 28. This plurality of handle slits 28 enables the bodily fluids sample collection device 10 to be attached to the patient's 40 clothing or to another prop to allow for additional support. This plurality of handle slits 28 allows for attachment and support when the patient 40 is camping and during other outside activities. In an alternative embodiment of the present invention, shown in FIG. 6, each of the handles 23 may comprise a plurality of ribs 53, to provide the patient 40 or medical practitioner with gripping stability and security.

As depicted in FIGS. 1 and 4, the bodily fluids sample collection 10 device of the present invention, as disclosed, provides a an elastic elongated frame member 20 for supporting and securing a bodily fluids sample cup 30. The lid 33 is removed from the sterile bodily fluids sample cup 30, which would be kept sterile by the medical clinic or other provider. As shown in FIG. 1, the bodily fluids sample cup 30 is placed in the center or cup securing region 26 of the elastic elongated frame member 20 in the pair of opposing semi-circular cup holding portions 34 of the elastic elongated frame member 20. As depicted in FIG. 4, the elastic elongated frame member 20 is either placed on the toilet seat 43 of the toilet bowl 41 or held by the patient 40, medical service provider, by the plurality of attachable handle slits 28 or by the plurality of ribs 53.

As shown in FIGS. 2-4, the elastic elongated frame member 20 has a frame length 27 extending beyond the edge 42 of the toilet seat 43 or the toilet bowl 41. The patient 40 fills the bodily fluids sample cup 30 with a bodily fluids sample 35 or other specimen and without removing or touching the bodily fluids sample cup 30, places the lid 33 back on the bodily fluids sample cup 30 and returns it to the medical service provider.

The elastic elongated frame member 20 of the present invention, being made of plastic or other lightweight durable and inexpensive material, can either be thrown away, recycled, or sanitized, and reused.

The bodily fluids sample collection device 10 of the present invention is very maneuverable. The frame of the device is sturdy and can hold a bodily fluids sample cup 30 full of specimen without collapsing or having the patient 40 drop the bodily fluids sample cup 30.

The bodily fluids sample collection device 10 of the present invention with the elastic elongated frame member 20 and bodily fluids sample cup 30 can be used by medical service providers when instructed to collect a bodily fluids sample from a child. Veterinarians or pet owners may use the present invention to collect bodily fluids samples from dogs and other pets.

This bodily fluids sample collection device 10 of the present invention can be safely and effectively used in hospitals, medical clinics, medical labs, military facilities, drug rehabilitation centers, police stations, prisons, group homes, Senior and Alzheimer's Centers/facilities, private homes, and facilities with children, special needs children, and adults.

The present invention will also be helpful to men as patients 40 if providers ask for a midstream sample catch. Since the first frame side 24 and the opposing second frame side 25 of the elastic elongated frame member 20 of the present invention are flexible, it is easy for a male patient 40 to pinch together the first frame side 24 and the opposing second frame side 25 and collect the bodily fluids sample without touching the bodily fluids sample cup 30; thereby, keeping both the patient's 40 hands and the sample clean.

Figure 7:
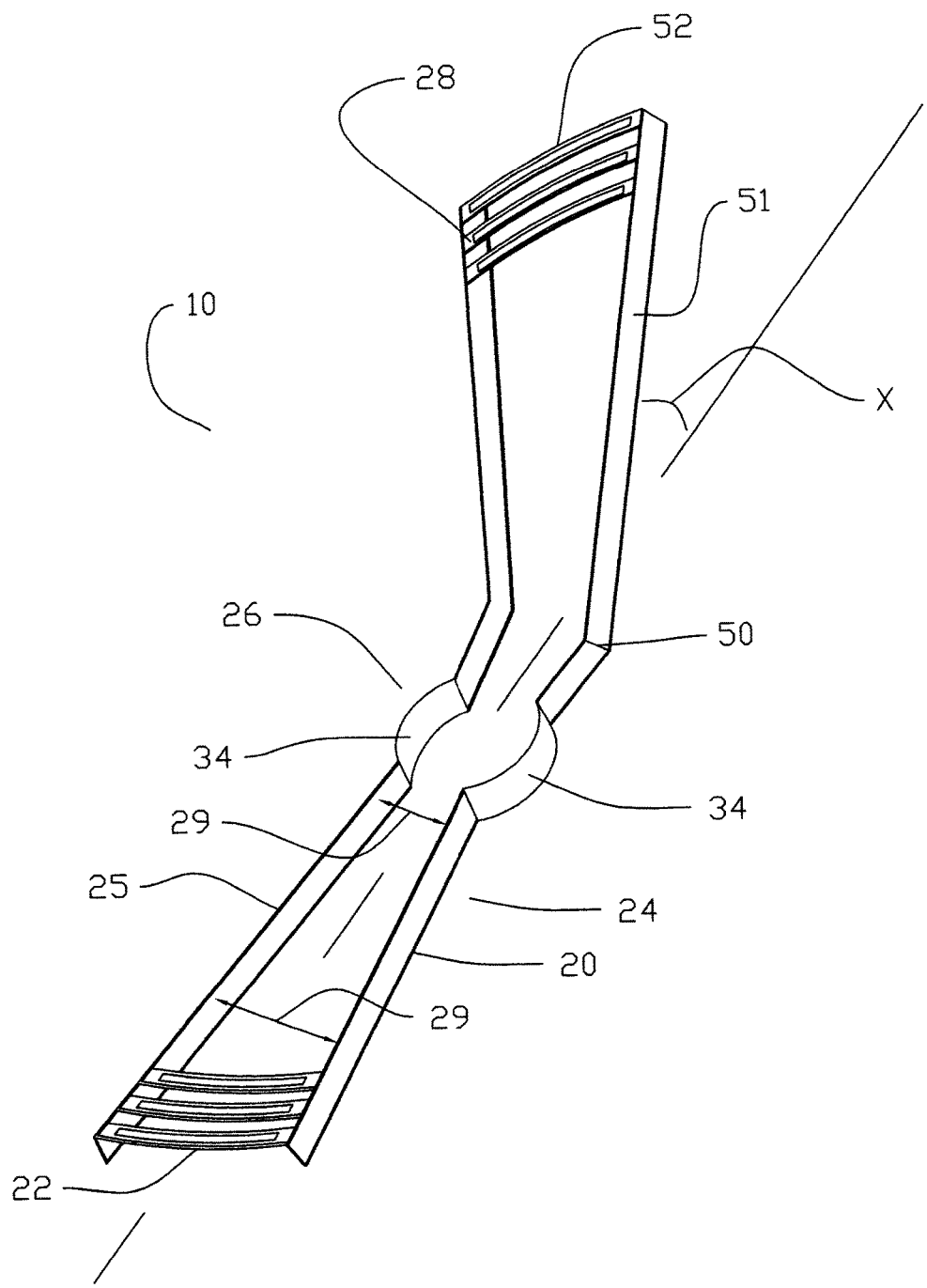
FIG. 7 illustrates a perspective elevation view of one embodiment of the present invention, depicting the bodily fluids sample collection device having a collection handle.

When a mid-stream sample is requested to be collected, frequently some of the urine or other bodily fluids sample 35 invariably ends up on the elastic elongated frame member 20 or bodily fluids sample cup 30 of the bodily fluids collection device 10 shown in FIGS. 4 and 7. The patient 40 or medical service provider does not want to contaminate the bodily fluids sample 35 or to touch the bodily fluids 35 which did not end up in the bodily fluids sample cup 30. The present invention, as shown in FIG. 1, allows the lid 33 to be placed on the bodily fluids sample cup 30 without the patient 40 or other individual touching the bodily fluids sample cup 30 before the bodily fluids sample 35 is secured within. As well, the patient 40 does not touch the toilet bowl 41 or the toilet seat 43.

As far as using the present invention for animals, and for dogs, in particular as "patients", the same use is applied that is used for male patients 40.

The bodily fluids sample collection device 10 of the present invention can be used for collecting specimens from children, as noted above, and for other persons with special needs, by having the medical service provider hold the bodily fluids sample collection device 10 at the first end 22 or the opposing second end 21, pinching the first frame side 24 and the opposing second frame side 25 together, preferably with thumb and forefinger, to provide a clean and stable holder (medical service provider) to collect the bodily fluids sample 35 from the patient 40.

Figure 5:
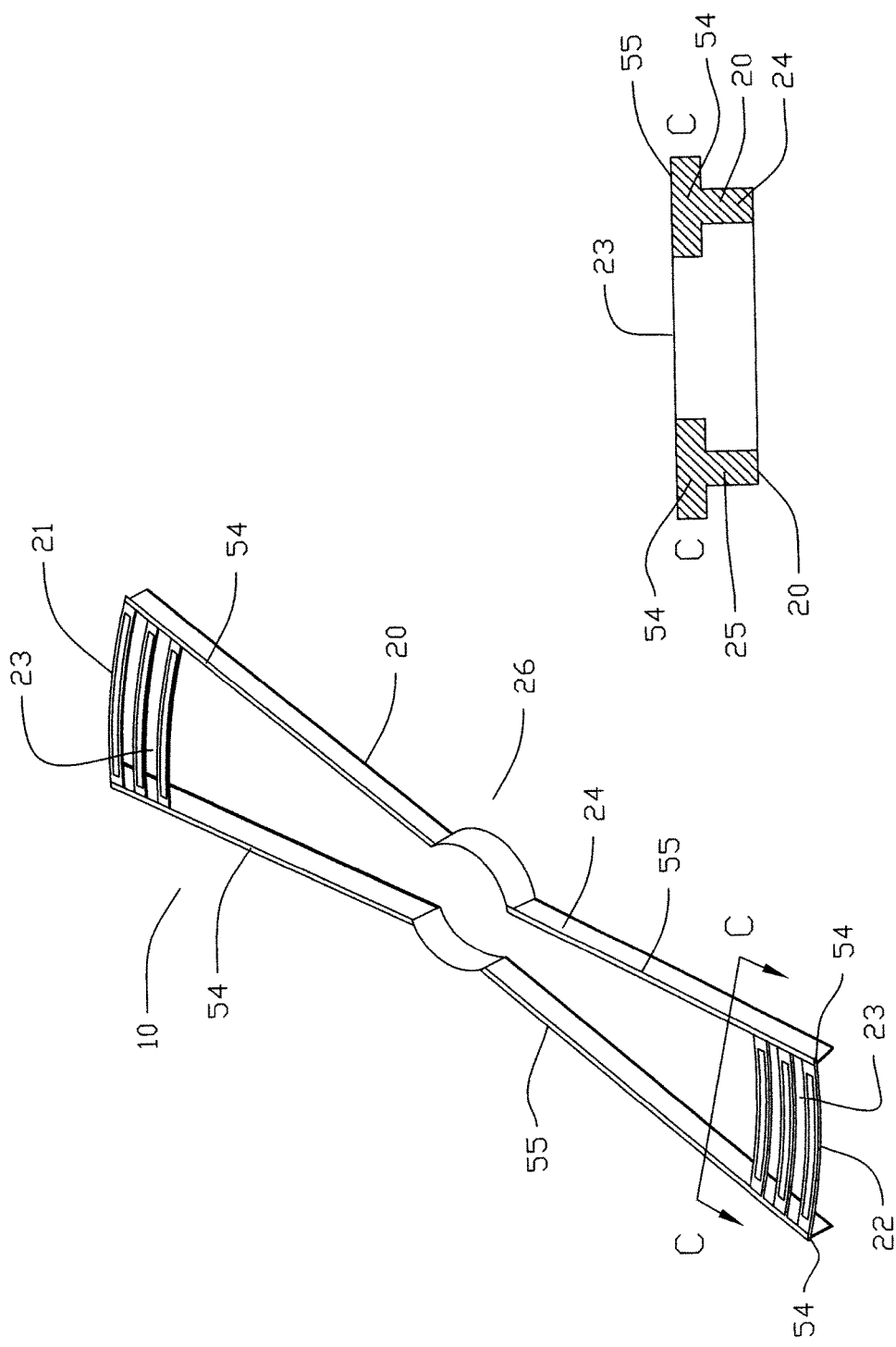
FIG. 5 illustrates a perspective elevation view of one embodiment of the present invention, having a cross section C-C' of a plurality of top flange members.

In another embodiment of the present invention, as depicted in FIGS. 5 and 5A, the elastic elongated frame member 20 of the bodily fluids sample collection device 10 further comprises a plurality of top flange members 54 positioned along the top edge 55 of the elastic elongated frame member 20, shown in cross section C-C of FIG. 5, as detailed in FIG. 5A. Each of the plurality of top flange members 54 runs along the top edge 55 from the cup securing region 26 to each, respective handle 23 of the bodily fluids collection device 10. The plurality of top flange members 54 provide support and comfort to the patient 40 when the patient 40 is seated upon the bodily fluids sample collection device 10 for collecting a bodily fluids sample 35 or other sample.

Figure 8:
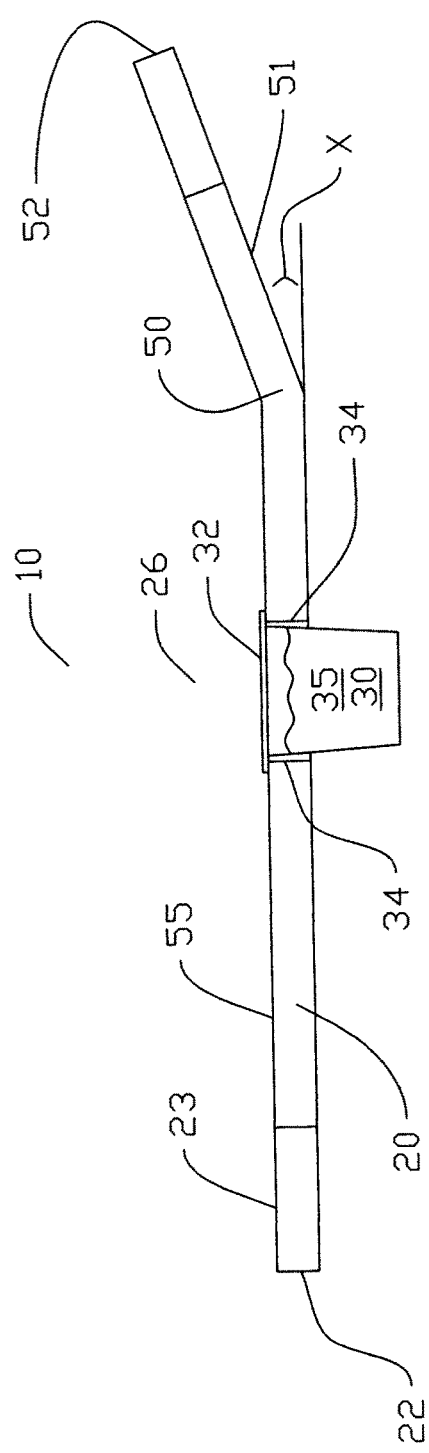
FIG. 8 illustrates a side elevation planar view of the bodily fluids sample collection device having a collection handle, in one embodiment of the present invention.

As depicted in FIGS. 7 and 8, a perspective elevation view and a side elevation view, respectively, in an alternative embodiment of the present invention, the bodily fluids sample collection device 10 comprises an elastic elongated frame member 20 comprising a first end 22 and an opposing second handle end 50. The elastic elongated frame member 20 is planar from the first end 22 to the opposing second handle end 50. As shown in FIG. 8, the bodily fluids sample cup 30 is presented as flush or "even" with the elastic elongated frame member 20 when set in place in the elastic elongated frame member 20 with a lid 33 removed. This feature of the present invention allows the patient to sit on the bodily fluids sample collection device 10, or alternatively, not to do so, in either case to facilitate effective and accurate sample collecting, particularly as between use by female and male patients 40, as noted above.

As shown in FIGS. 7 and 8, in an alternative embodiment of the present invention, the elastic elongated frame member 20 further comprises a collection handle 51 obliquely attached to the elastic elongated frame member 20 at the opposing second handle end 50, and a collection handle end 52 on the collection handle 51 opposing the opposing second handle end 50, as well as a first frame side 24 and an opposing second frame side 25. The obliquely angled bodily fluids collection sample device 10, (depicted in FIGS. 7 and 8 by the oblique angle to the horizontal or plane labeled as X of this embodiment allows for more convenient use by male patients and for use with animals.

Figure 6:
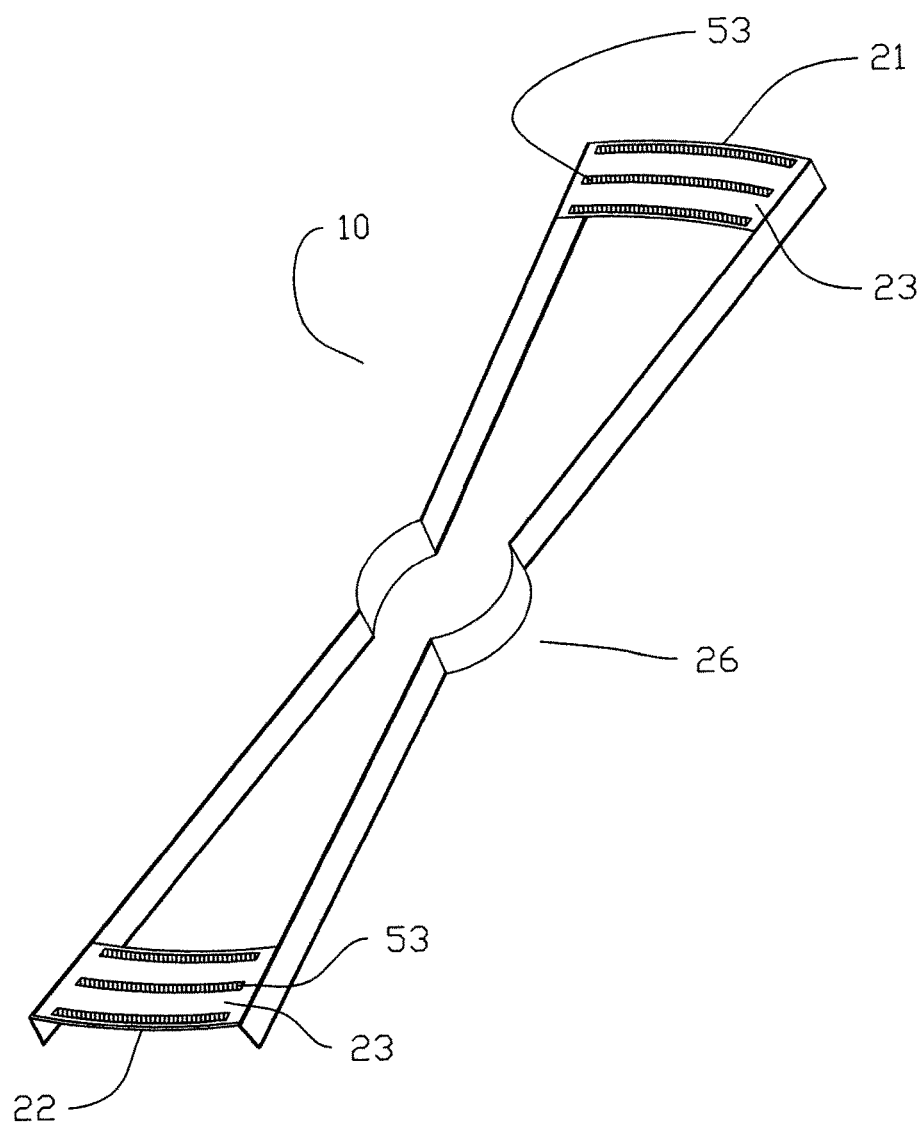
FIG. 6 illustrates a perspective elevation view of one embodiment of the present invention, with the handles comprising a plurality of ribs.

In the alternative embodiment of the present invention depicted in FIGS. 7 and 8, the first frame side 24 and the opposing second frame side 25 angle inward beginning concurrently from the first end 22 and the opposing second collection handle end 52, toward a cup securing region 26 centrally located in the elastic elongated frame member 20 and increasingly narrowing a frame width 29 between the first frame side 24 and the opposing second frame side 25, as shown in FIGS. 2 and 6. The first frame side 24 and the opposing second frame side 25 at the cup securing region 26 having the pair of opposing semi-circular cup holding portions 34 being flexibly adapted to securely receive and support a bodily fluids sample cup 30 disposed in an upright position 31 between the first frame side 24 and the opposing second frame side 25 of the elastic elongated frame member 20, to collect a bodily fluids sample 35 or other excrement sample, as depicted earlier in FIGS. 1, 1A, and 4. The first frame side 24 and the opposing second frame side 25 at the cup securing region 26 are flexibly adapted for easy placement and release of the bodily fluids sample cup 30 by a patient 40, the same manner and operation as noted above. The collection handle 51 enables the patient 40 to grasp the bodily fluids sample collection device 10. The bodily fluids sample cup 30 is supported in the cup securing region 26 and has a top 32 located planarly with the elastic elongated frame member 20. The pair of opposing semi-circular cup holding portions 34 is adjustable to securely receive and support bodily fluids sample cups 30 of differing sizes, and are adjustable to securely receive and support bodily fluids sample cups 30 of differing sizes.

The collection handle end 52, as shown in FIGS. 7 and 8 in this alternative embodiment of the present invention enables the patient 40 to grasp the bodily fluids sample collection device 10 distally, or away, from the bodily fluids sample cup 30, for sanitary purposes. The collection handle end 52 in the alternative embodiment shown in FIG. 7 comprises a plurality of attachable handle slits 28. In an alternate embodiment of the present invention, the collection handle end 52 comprises a plurality of ribs, as depicted with the handles 23 in another embodiment in FIG. 6.

Having thus described in detail a preferred selection of embodiments of the present invention, it is to be appreciated, and will be apparent to those skilled in the art, that many physical changes could be made in the device without altering the invention, or the concepts and principles embodied therein. Unless otherwise specifically stated, the terms and expressions have been used herein as terms of description and not terms of limitation, and are not intended to exclude any equivalents of features shown and described or portions thereof. Various changes can, of course, be made to the preferred embodiment without departing from the spirit and scope of the present invention. The present invention device, therefore, should not be restricted, except in the following claims and their equivalents.

I claim:

1. A bodily fluids sample collection device, comprising:
   (a) An elastic elongated frame member comprising: a first end and an opposing second end, the first end and the opposing second end each having a handle, the elastic elongated frame member being planar from the first end to the opposing second end;
   (b) The elastic elongated frame member further comprising: a top edge, a first frame side and an opposing second frame side, the first frame side and the opposing second frame side concurrently angling inward from the first end and the opposing second end, respectively, from each handle toward a cup securing region centrally located in the elastic elongated frame member, and the elastic elongated frame member thereby having an increasingly narrowing frame width between the first frame side and the opposing second frame side toward the cup securing region, and a bodily fluids sample cup disposed in an upright position between the first frame side and the opposing second frame side of the elastic elongated frame member for receiving a bodily fluids sample from a patient;
   (c) the first frame side and the opposing second frame side at the cup securing region each having an opposing, flexibly adjustable semi-circular cup holding portion, comprised of a pair of opposing semi-circular cup holding portions, defining the cup securing region of the elastic elongated frame member, the first frame side and the opposing second frame side being flexibly adapted to securely and removably engage, receive and support the bodily fluids sample cup;
   (d) the first frame side and the opposing second frame side at the cup securing region being flexibly adapted for easy placement and release of the bodily fluids sample cup by the patient;
   (e) a toilet bowl;
   (f) the elastic elongated frame member having a frame length extending beyond an edge of the toilet bowl;
   (g) the toilet bowl having a major axis and a minor axis; and
   (h) whereby the handles enable the patient to grasp the bodily fluids sample collection device.

2. The bodily fluids sample collection device of claim 1 comprising: the toilet bowl freely supporting the elastic elongated frame member being configured and oriented along the minor axis of the toilet bowl, having the frame length of the elastic elongated frame member extending beyond minor outer edges of the toilet bowl.

3. The bodily fluids sample collection device of claim 1 further comprising: a toilet seat hingedly attached to the edge of the toilet bowl and freely supporting the elastic elongated frame member.

4. The bodily fluids sample collection device of claim 1, wherein each handle of the respective first end and the opposing second end enables the patient to grasp the elastic elongated frame member without touching the toilet seat or the toilet bowl and distally from the bodily fluids sample cup.

5. The bodily fluids sample collection device of claim 1, wherein each handle of the respective first end and the opposing second end comprises a plurality of attachable handle slits.

6. The bodily fluids sample collection device of claim 1, wherein the bodily fluids sample cup is supported in the cup securing region, the bodily fluids sample cup having a top located generally planarly within, and slightly above, the elastic elongated frame member and having a lid, the lid having a fastening means for securing the lid to the top of the bodily fluid sample cup.

7. The bodily fluids sample collection device of claim 1, wherein the fastening means to the lid includes at least one of opposing threads, a clip, or a snap-on lid.

8. The bodily fluids sample collection device of claim 1, wherein the pair of opposing semi-circular cup holding portions of the elastic elongated frame member being elastically adjustable to securely receive and support bodily fluids sample cups of differing sizes.

9. The bodily fluids sample collection device of claim 1, wherein the elastic elongated frame member further comprises: a plurality of top flange members positioned along the top edge located on the first frame side and the opposing second frame side of the elastic elongated frame member.

10. The bodily fluids sample collection device of claim 1, wherein each handle of the respective first end and the opposing second end comprises a plurality of ribs.

11. The bodily fluids sample collection device of claim 1, the elastic elongated frame member being configured and oriented along the major axis of the toilet bowl.

12. The bodily fluids sample collection device of claim 1, wherein the pair of opposing semi-circular cup holding portions of the elastic elongated frame member being inwardly sloping from the top edge of the elastic elongated frame member toward the cup securing region.

13. A bodily fluids sample collection device, comprising:
(a) an elastic elongated frame member comprising: a first end and an opposing second handle end;
(b) the elastic elongated frame member being planar from the first end to the opposing second handle end;
(c) the elastic elongated frame member further comprising: a collection handle obliquely attached to the elastic elongated frame member at the opposing second handle end, the collection handle having a collection handle end opposing the opposing second handle end;
(d) the elastic elongated frame member further comprising: a first frame side and an opposing second frame side, the first frame side and the opposing second frame side angling inward beginning concurrently from the first end and the collection handle end, toward a cup securing region centrally located in the elastic elongated frame member and increasingly narrowing a frame width between the first frame side and the opposing second frame side toward the cup securing region and a bodily fluids sample cup disposed in an upright position between the first frame side and the opposing second frame side of the elastic elongated frame member for receiving a bodily fluids sample from a patient;
(e) the first frame side and the opposing second frame side at the cup securing region each having an opposing, flexibly adjustable semi-circular cup holding portion comprised of a pair of opposing semi-circular cup holding portions, defining the cup securing region of the elastic elongated frame member, the first frame side and the opposing second frame side being flexibly adapted to securely receive and support the bodily fluids sample cup disposed in an upright position between the first frame side and the opposing second frame side of the elastic elongated frame member;
(f) the first frame side and the opposing second frame side at the cup securing region being flexibly adapted for easy placement and release of the bodily fluids sample cup by the patient; and
(g) whereby the collection handle enables the patient to grasp the bodily fluids sample collection device.

14. The bodily fluids sample collection device of claim 13, wherein the bodily fluids sample cup is supported in the cup securing region, the bodily fluids sample cup having a top located generally planarly within, and slightly above, the elastic elongated frame member and having a lid, the lid having a fastening means for securing the lid to the top of the bodily fluid sample cup.

15. The bodily fluids sample collection device of claim 13, wherein the fastening means to the lid includes at least one of opposing threads, a clip, or a snap-on lid.

16. The bodily fluids sample collection device of claim 13, wherein the collection handle end is configured to enable the patient to grasp the bodily fluids sample collection device distally from the bodily fluids sample cup.

17. The bodily fluids sample collection device of claim 13, wherein the collection handle end comprises a plurality of attachable handle slits.

18. The bodily fluids sample collection device of claim 13, wherein the pair of opposing semi-circular cup holding portions being adjustable to securely receive and support bodily fluids sample cups of differing sizes.

19. The bodily fluids sample collection device of claim 13, wherein the collection handle end comprises a plurality of ribs.

20. The bodily fluids sample collection device of claim 13, wherein the pair of opposing semi-circular cup holding portions of the elastic elongated frame member being inwardly sloping from the top edge of the elastic elongated frame member toward the cup securing region.

* * * * *